United States Patent [19]

Biftu

[11] Patent Number: 4,757,084

[45] Date of Patent: Jul. 12, 1988

[54] 2,5-DIARYL TETRAHYDROTHIOPHENES AND ANALOGS THEREOF AS PAF-ANTAGONISTS

[75] Inventor: Tesfaye Biftu, Old Bridge, N.J.

[73] Assignee: Merck & Co., Inc., Rahway, N.J.

[21] Appl. No.: 776,191

[22] Filed: Sep. 13, 1985

Related U.S. Application Data

[63] Continuation of Ser. No. 584,693, Feb. 29, 1984, abandoned.

[51] Int. Cl.⁴ .................... A61K 31/38; C07D 333/12
[52] U.S. Cl. ........................................ 514/438; 549/75; 549/77; 549/78; 549/79; 549/80
[58] Field of Search .................. 549/80, 59, 60, 62, 549/64, 66, 67, 70, 71, 72, 73, 74, 75, 77, 78, 79, 87; 514/438

[56] References Cited

U.S. PATENT DOCUMENTS 2,439,345  4/1948  Morris ................................. 549/87
3,644,399  5/1969  Brown et al. .
3,655,692  4/1972  Shen .................................... 549/71

OTHER PUBLICATIONS

Parnes, Chem. Abst. 90: 87166p (1979).
Biftu et al., J. Chem. Soc. 1147 (1978).
Biftu et al., J. Chem. Soc. 2276 (1979).

Primary Examiner—Alan Siegel
Attorney, Agent, or Firm—Theresa Y. Cheng; Michael C. Sudol

[57] ABSTRACT

Analogs of 2,5-Diaryl tetrahydrothiophenes which were substituted or unsubstituted on 3,4-positions were prepared.

These compounds are found to be leukotriene inhibitors and potent and specific PAF (Platelet Activating Factor) antagonists. They are therefore useful in the treatment of various diseases or disorders mediated by the leukotriene and/or PAF, for example, inflammation, cardiovascular disorder, asthma; lung edema, adult respiratory distress syndrome, pain, and aggregation of platelets.

9 Claims, No Drawings

2,5-DIARYL TETRAHYDROTHIOPHENES AND ANALOGS THEREOF AS PAF-ANTAGONISTS

This application is a continuation of Ser. No. 584,693 filed 2/29/84 and now abandoned.

BACKGROUND OF THE INVENTION

Platelet-activating factor (PAF) has recently been identified as an acetyl glyceryl ether phosphorylcholine (AGEPC), i.e., 1-O-hexadecyl/octadecyl-2-acetyl-sn-glyceryl-3-phosphorylcholine (Hanahan D. J., et al., *J. Biol. Chem.* 255:5514, 1980). Even before its chemical identification, PAF had been linked to various biological activities and pathways making it one of the important mediators responsible for a variety of physiological processes including activation or coagulation of platelets, pathogenesis of immune complex deposition, smooth muscle contraction, inflammation, pain, edema as well as respiratory, cardiovascular and intravascular alterations. Since these physiological processes are in turn associated with a large group of diseases, for example, inflammatory disease, cardiovascular disorder, asthma, lung edema, and adult respiratory distress syndrome, more and more scientific investigation has been focused on the search of a PAF-antagonist or inhibitor for treating or preventing these common diseases. Furthermore, the compounds of the present invention are found to be leukotriene inhibitors.

Substituted tetrahydrothiophenes can exist in six different stereoisomers as shown in Scheme I.

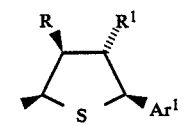 (1)

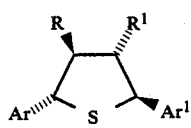 (2)

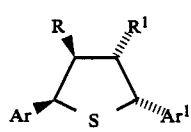 (3)

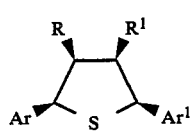 (4)

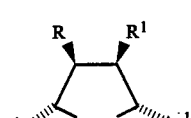 (5)

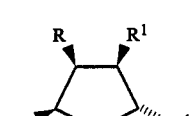 (6)

We have been able to prepare all the possible isomers of the tetrahydrothiophene analogs with different substituents and found that there exists a structure-activity relationship favoring the trans isomer of formula

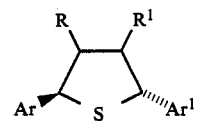

when R and $R^1$ are both hydrogen.

Accordingly, it is the object of the present invention to prepare the most potent isomers of known or novel tetrahydrothiophene derivatives as PAF-antagonists and leukotriene inhibitors and use them for the treatment of various diseases including prevention of platelet aggregation, hypertension, inflammation, asthma, lung edema, adult respiratory distress syndrome, cardiovascular disorder and other related skeletal-muscular disorders.

Another object of the present invention is to develop processes for the preparation of each and every stereoisomer of the 2,5-diaryltetrahydrothiophene analogs.

A further object of the present invention is to provide acceptable pharmaceutical compositions containing one or more of the tetrahydrothiophene derivatives and/or analogs as the active ingredient. As PAF-antagonists, these novel compositions should be effective in the treatment of various skeletal-muscular related diseases.

Finally, it is the ultimate object of this invention to provide a method of treatment comprising the administration of a therapeutically sufficient amount of these PAF antagonists to a patient suffering from various skeletal-muscular disorders including inflammation, e.g., osteoarthritis, rheumatoid arthritis and gout, hypertension, asthma, pain, lung edema, or adult respiratory distress syndrome or cardiovascular disorder.

DETAILED DESCRIPTION OF THE INVENTION

A. Scope of the Invention

This invention relates to compounds of formula

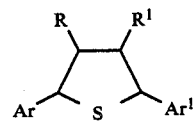 (I)

wherein R and $R^1$ independently are
(a) hydrogen;
(b) lower alkyl or cycloalkyl of 1–6 carbon atoms, e.g., methyl, cyclopropylmethyl, ethyl, isopropyl, butyl, pentyl or hexyl;
(c) haloloweralkyl especially $C_{1-6}$ haloalkyl, for example, trifluoromethyl;
(d) halo especially fluoro;
(e) COOH;
(f) $CONR^2R^3$ wherein $R^2$ and $R^3$ independently represent $C_{1-6}$ alkyl and hydrogen;
(g) $COOR^2$;
(h) loweralkenyl especially $C_{1-6}$ alkenyl e.g., vinyl, allyl, $CH_3CH=CH-CH_2-CH_2$, or $CH_3(CH_2)_3CH=CH-$;
(i) $-COR^2$;
(j) $-CH_2OR^2$;
(k) loweralkynyl especially $C_{1-6}$ alkynyl e.g., $-C\equiv CH$;
(l) $-CH_2NR^2R^3$;

(m) —CH$_2$SR$^2$;
(n) =O; or
(o) —OR$^2$;

Ar and Ar$^1$ are the same or different from each other and are (a) phenyl or substituted phenyl of formula

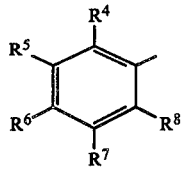

where R$^4$–R$^8$ independently represents H, RO—, R$^2$S—, R$^2$SO—, R$^2$SO$_2$—, CF$_3$O—, CF$_3$S—, CF$_3$SO—, CF$_3$SO$_2$—, R$^2$R$^3$N—, —OCH$_2$CO$_2$R$^2$, —NR$^2$COR$^3$, —O—CONH$_2$, CONR$^2$R$^3$, —CR$^2$R$^3$R$^4$, —SO$_2$NR$^2$R$^3$, —CO$_2$R$^2$, NR$^2$SO$_2$R$^3$, COR$^2$, NO$_2$, or CN. For example, 3-methoxy-4-allyloxy-5-acetamidophenyl, 3-methoxy-4-cyclopropylmethyl-5-benzamide, 3,4-dimethoxyphenyl, 3,5-dimethoxy-4-dimethylaminophenyl, 3,4,5-trimethoxyphenyl or R$^4$-R$^5$, R$^5$-R$^6$, R$^6$-R$^7$ and R$^7$-R$^8$ are joined together and form a bridge, for example, —OCH$_2$O—, —OCH$_2$CH$_2$—O— or —OCH$_2$CH$_2$N—;

(b) pyrryl or substituted pyrryl;
(c) furyl or substituted furyl;
(d) pyridyl or substituted pyridyl and salts thereof;
(e) thiophene or substituted thiophene;
(f) cyclohexyl or substituted cyclohexyl; or
(g) pyrimidyl or substituted pyrimidyl and salts thereof. Also, the sulfur of the tetrahydrothiophene could easily be converted to the corresponding sulfoxide or sulfone.

The compound of formula (I) can exist in the six isomers as described in Scheme I. These various isomers bear a close relationship to the PAF-antagonistic activity observed for the compounds within the scope of this invention.

Preferably, the PAF-antagonists of this invention are of structural formula

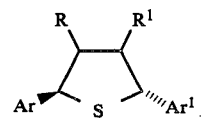

wherein R, R$^1$, Ar and Ar$^1$ are as previously defined, an enantiomer thereof and salts where applicable.

The most active PAF-antagonists discovered by us to date are the trans-2-(3,4,5-trimethoxyphenyl)-5-(5,6-dimethoxy-3-pyridyl)tetrahydrothiophene and the trans isomer of 2,5-bis-(3,4,5-trimethoxyphenyl)tetrahydrothiophene.

B. Preparation of the compounds within the scope of the invention

The PAF-antagonists of this invention have been prepared from diaroylbutanes as indicated in the following schemes.

The tetrahydrothiophenes were prepared from 1,4-diols or 1,4-dihalides by cyclization with appropriate reagents. The diols are in turn made by reduction of 1,4-diketones with the usual reducing agents. The diketones were made by oxidative coupling of enolates prepared from acetophenone or propiophenone derivatives, reaction of enolates generated from propiophenone or acetophenones with α-halo ketones or by the Stetter reaction as shown below in Scheme a.

Scheme a

Synthesis from diaroylbutanes, for example:

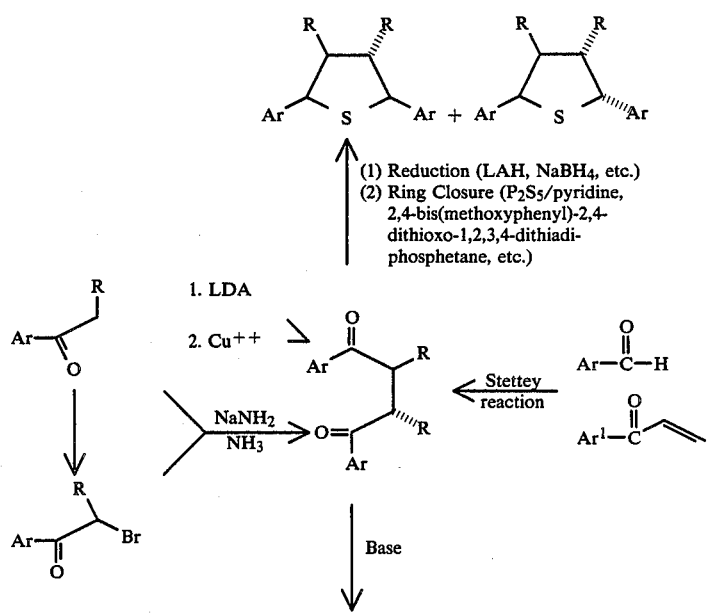

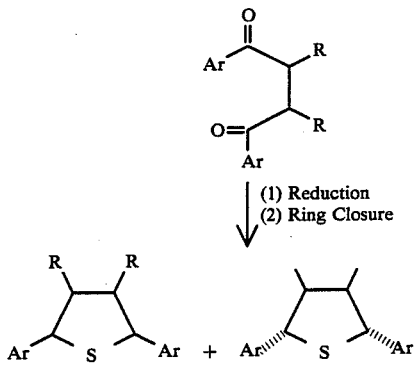

(1) Reduction
(2) Ring Closure

C. Utility of the compounds within the scope of the invention

This invention also relates to a method of treatment for patients (or mammalian animals raised in the dairy, meat, or fur industries or as pets) suffering from disorders or diseases which can be attributed to PAF and/or leukotriene and more specifically, a method of treatment involving the administration of the PAF-antagonists of formula (I) as the active constituents.

Accordingly, the compounds of Formula (I) can be used among other things to reduce pain and inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by the PAF, the compounds of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed.

Dosage levels of the order of from about 0.1 mg to about 140 mg per kilogram of body weight per day are useful in the treatment of the above-indicated conditions (about 5 mg to about 7 gms. per patient per day). For example, inflammation may be effectively treated by the administration of from about 0.2 to 50 mg of the compound per kilogram of body weight per day (about 20 mg to about 3.5 gms per patient per day). Preferably a dosage of from about 1 mg to about 20 mg per kilogram of body weight per day may produce good results (about 25 mg to about 1 gm per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

D. Bioassay Results Supporting the utility of the compounds of the present invention It has been found that the compounds of formula (I) exhibit in vitro and in vivo antagonistic activities with respect to PAF:

A. In Vitro Assay: In vitro, they inhibit PAF-induced functions in both the cellular and tissue levels by disturbing the PAF binding to its specific receptor site. The ability of a compound of formula (I) to inhibit the PAF binding to its specific receptor binding site on rabbit platelet plasma membranes was measured by an assay recently developed by us.

The inhibition of $H^3$-PAF binding to the rabbit platelet plasma membrane by a PAF-antagonist of Formula (I) was determined by a method employing isotopic labeling and filtration techniques. Generally, a series of Tris-buffered solutions of the selected antagonist at predetermined concentrations were prepared. Each of these solutions contains 1 pmole of $^3$H-PAF, a known amount of the test antagonist, and a sufficient amount of the pH 7.5 Tris-buffer solution (10 mM Tris, 0.25% bovine serum albumin, and 150 mM NaCl per ml water) to make the final volume of 1 ml. After adding into a set of test tubes each with 100 $\mu$g of the platelet plasma membrane suspension (S. B. Hwang, et al., *Biochemistry*, 1983) and one of the Tris-buffer solutions described above, the resulting mixture in each test tube was incubated at 0° C. for about one hour or until the reaction was complete. Two control samples, one of which ($C_1$) contains all the ingredients described above except the antagonist and the other ($C_2$) contains $C_1$ plus a 1000-fold excess of unlabeled PAF, were also prepared and incubated simultaneously with the test samples. After the incubation was completed, the contents of each test tube were filtered under vacuo through a Whatman GF/C fiberglass filter and the residue washed rapidly several times with a total of 20 ml cold (0°–5° C.) Tris-buffer solution. Each washed residue was then suspended in 10 ml scintillation solution (Aquasol 2, New England Nuclear, Connecticut) and the radioactivity was counted in a Packard Tri-Carb 460CD Liguid Scintillation System. Defining the counts from a test sample as "Total binding with antagonist"; the counts from the control sample $C_1$, as "Total binding $C_1$"; and the counts from the control sample $C_2$ as "nonspecific binding $C_2$", the percent inhibition of each test antagonist can be determined by the following equation:

$$\% \text{ Inhibition} = \frac{(\text{Total binding } C_1) - \left(\begin{array}{c}\text{Total binding} \\ \text{with antagonist}\end{array}\right)}{\text{Specific binding}} \times 100$$

-continued $$\text{Specific binding} = \text{(Total binding } C_1) - \text{(non-specific binding } C_2)$$

From our observation, compounds of formula (I) inhibit in vitro PAF-induced platelet aggregation (rabbit or human platelets); PAF-induced guinea pig peritoneal PMN (polymorphonuclear leukocytes) aggregation; PAF-induced human PMN secretion; and PAF-induced guinea pig smooth muscle contraction although they are not $H_2$-receptor antagonists. They are also shown in these inhibition studies to be highly specific to PAF. For example, they do not inhibit the binding of $H_1$ antagonist ($^3$H-pyrilamine) to guinea pig brain membrane, nor do they inhibit the binding of a cholecystokinin (CCK) receptor based on an assay on isolated rat pancreas membrane. Furthermore, they affect no or only minute inhibition on the histamine-induced ileum contraction from guinea pigs.

Results from the In Vitro assay

The antagonistic activity of the compounds of structural formula (I) is summarized in the following table:

5. One and a quarter hours after dosing, cannulate surgically the left femoral vein and artery of the rat.

6. One and a half hours after dosing, infuse through cannulated vein 0.5 nannomoles (n moles) per 200 g body weight of the rat. Take blood samples from the cannulated femoral artery at 1.5, 3, 5, 8, 11, 15, 20 25 and 30 minute intervals. After the beginning of the PAF infusion as well as just before the PAF infusion, measure the following three parameters for each blood sample:
  (a) the arterial blood flow rate: determined by measuring the time to fill a pre-calibrated 14 μl capillary tube;
  (b) the vascular permeability: measured by calculating the increased hematocrit which results from loss of plasma from the circulation to extra-vascular spaces.
  (c) the circulatory degranulation: determined by assaying the increased plasma level of N-acetyl-glucosaminidase, a marker lysosomal enzyme.

7. Determine the percent change in each parameter of a blood sample at each post-PAF interval including the 30 minute interval, relative to the pre-PAF blood values.

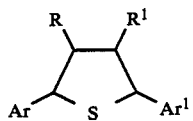

| R | $R^1$ | Ar | $Ar^1$ | Isomer | dose(μM) | % inhibition |
|---|---|---|---|---|---|---|
| H | H | 3,4-dimethoxyphenyl | same as Ar | trans | 1 | 100 |
|   |   |                     |            |       | .3 | 83 |
|   |   |                     |            |       | .1 | 43 |
|   |   |                     |            |       | .03 | 31 |
| H | H | 3,4-dimethoxyphenyl | same as Ar | cis | 1 | 62 |
|   |   |                     |            |     | .3 | 41 |
|   |   |                     |            |     | .1 | 25 |
| H | H | 3,4,5-trimethoxyphenyl | same as Ar | trans | 1 | 100 |
|   |   |                        |            |       | .3 | 100 |
|   |   |                        |            |       | .1 | 95 |
|   |   |                        |            |       | .03 | 69 |
| $CH_3$ | $CH_3$ | 3,4-dimethoxyphenyl | same as Ar | (1) | 5 | 82 |
|        |        |                     |            |     | 1 | 53 |
| $CH_3$ | $CH_3$ | 3,4-dimethoxyphenyl | same as Ar | (3) | 1 | 82 |
|        |        |                     |            |     | .3 | 43 |
|        |        |                     |            |     | .1 | 68 |
|        |        |                     |            |     | .03 | 30 |
| H | H | 3,4,5-trimethoxyphenyl | 5,6-dimethoxy-3-pyridyl |  | 5 | 96 |
|   |   |                        |                         |  | 1 | 80 |

B. In vivo Assay: Protocol for Assay of Oral Activity of PAF-antagonists in inhibiting PAF-induced symptoms including decreased arterial blood flow, increased vascular permeability and increased degranulation in rats Animals: Female, Wiston rats, 190–220 g
Procedure:
1. Fast rats overnight.
2. Weigh the rats the morning after fasting.
3. Suspend a test compound in 0.5% methylcellulose with 12 ounce hand homogenizer or a sonicator if necessary to yield a fine suspension. Administer orally each of the rats with 2 ml of suspension such that the rat received a predetermined amount of the compound varying between 2 and 50 mg compound per kg body-weight of the rat.
4. One hour after dosing, anesthetize the rat with sodium Nembutal (i.p.).

8. Calculate the percent inhibition by the formula:

$$\% \text{ inhibition} = 100\% \times \frac{\% \text{ change without test compound} - \% \text{ change with test compound}}{\% \text{ change without test compound}}$$

Results:
Listed in the following table are the % inhibition of the PAF-induced responses at different oral doses of certain representative compounds.

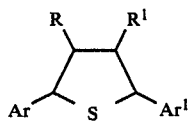

| R | R¹ | Ar | Ar¹ | Isomer | dose (mg/kg) | % inhibition A | B |
|---|----|----|----|--------|--------------|---|---|
| H | H | 3,4,5-tri-methoxyphenyl | same as Ar | trans | 40 | 81 | 81 |
|   |   |                          |            |       | 20 | 85 | 83 |
|   |   |                          |            |       | 5  | 58 | 60 |
|   |   |                          |            |       | 1  | 20 | 49 |
| H | H | 3,4-di-methoxyphenyl | same as Ar | cis | 20 | 41 | 35 |

A = increased vascular permeability
B = increased degranulation

Method B: Protocol for Assay of Oral Activity of PAF antagonists in inhibiting soluble immune complex induced effects including decreased arterial blood flow, increased vascular permeability and increased degranulation in rats.

Animals: Female, wistar rats, 190–22-g.
Procedure:
1. Fast rats overnight
2. Weigh the rats the morning after fasting
3. Suspend a test compound in 0.5% methylcellulose with 12 ounce hand homogenizer to yield fine suspension. Administer orally each of the rats with 2 ml of suspension such that the rat received a predetermined amount of the compound varying between 2 and 50 mg compound per kg bodyweight of the rat.
4. Soluble immune complexes (I.C.) were prepared by mixing 2.4 mg human serum albumin (HSA) with 51 mg of the Igby fraction from rabbit anti-HSA antiserum in a final volume of 3.4 ml and incubating at 37° C. for 1 hour. This ratio of HSA to antibody was previously determined to be in slight antigen excess of equivalence and to result in soluble I.C. Following 37° C. incubation, the I.C. was centrifuged at 10,000 xg, 5 minute and the resulting superinstant containing the soluble I.C. stored on ice.
5. Two and one-half hours after dosing, anesthetize the rat with sodium Nembutal (i.P.)
6. Two and three-quarters hours after dosing, cannulate surgically the left femoral vein and artery of the rat. Take a blood sample from the cannulated femoral artery before the I.C. infusion and 1.5, 3, 5, 8, 11, 15, 20, 25 and 30 minutes after the I.C. infusion. Measure the following three parameter for each blood sample:
   (a) the arterial blood flow rate: determined by measuring the time to fill a pre-calibrated 14 μl capillary tube;
   (b) the vascular permeability: measured by calculating the increased hematocit which results from loss of plasma from the circulation to extra-vascular spaces.
   (c) the circulatory degranulation: determined by assaying the increased plasma level of N-acetyl-glucosaminidase, a marker lysopomal enzyme.
8. Calculate the percent inhibition by the formula:

$$\% \text{ inhibition} = \frac{\left(\% \text{ change without test compound} - \% \text{ change with test compound}\right)}{\% \text{ change without test compound}} \times 100$$

Results:
Trans-2,5-bis(3,4,5-trimethoxyphenyl) tetrahydrothiophene at an oral dose of 50 mg/kg resulted in the following inhibitions of I.C. induced effects:

| Effect | % Inhibition |
|--------|--------------|
| Decreased arterial blood flow | 40% |
| Increased vascular permeability | 73% |
| Increased degranulation | 40% |

The following examples illustrate but do not define the present invention.

EXAMPLE 1

Step A: Preparation of trans and cis-2,5-bis (3,4-dimethoxyphenyl) tetrahydrothiophene In a 500 ml flask equipped with a stirrer and $N_2$, LDA was prepared from 20 ml THF, 10.1 g diisopropylamine and 62 ml 1.7m n-butyl lithium at −10° C. The temperature was dropped to −40° C. and then 18 g of 3,4-dimethoxyacetophenone in 40 ml THE added and stirring continues overnight.

500 ml of 1N HCL was added and the resulting precipitate collected by filtration. The brown ppt. was dissolved in methylene chloride and filtered through a bed of silica gel. Evaporation followed by crystallization from ethyl acetate gave 4.9 g of 1,2-bis(3,4-dimethoxybenzoyl)ethane as a white solid. M.p. 181°–182° C. NMR(CDCl$_3$) δ3.40 (4H, s, —COCH$_2$CH$_2$CO), 3.92(12H, s, OCH$_3$), 6.8–7.94 (6H, ArH).

In a similar manner, 26.2 g of 1,2-bis (3,4,5-trimethoxybenzoyl)ethane was prepared form 3,4,5-trimethoxyacetophenone (63 g), diisopropylamine (30.3 g) and 38.5 ml of n-butyl lithium (2.1 M).

Step B: Preparation of racemic-2,3-bis(3,4-dimethoxybenzoyl)butane

To 100 ml of liquid $NH_3$ and 100 mg $FeCl_3$, 1 g of sodium was added and stirred for 1 hr at −40° C. To that 7.7 g of 3,4-dimethoxypropiophenone was added and stirred for ½ hr. Eleven g of α-bromo-3,4-dimethoxypropiophenone was then added and stirring continued for 1½ hrs. At this point, 11 g of ammonium chloride and 200 ml of methylene chloride was added and the temperature allowed to rise to room temperature. Filtration, evaporation and crystalization of the residue from methanol gave 14.5 g of racemic-2,3-bis(3,4-dimethoxybenzoyl)butane as a white solid. NMR (CDCl$_3$) δ1.32(6H, d, J=7H$_z$), 3.92 and 3.94 (6H each, s, OCH$_3$, 6.8–7.8 (6H, ArH); m.p. 141°–142° C.

Step C: Preparation of Meso-2,3-bis (3,4-dimethoxybenzoyl)butane

One g of racemic 2,3-bis-(3,4-dimethoxybenzoyl)butane in 20 ml THF (warmed to dissolve) was treated with 50 mg of sodium methoxide in 2 ml methanol followed by 70 ml of ether and stirred overnight. The resulting precipitate was collected by filtration, dissolved in methylene chloride and chromatographed on silica gel column and eluted with ethylacetate-hexane (40:60) to afford meso-bis-(3,4-dimethoxybenzoyl)butane (206 mg) M.p. 188° C. Step D: Preparation of trans and cis-2,5-bis (3,4-dimethoxyphenyl)tetrahydrothiophene 1,2-Bis(3,4-dimethoxybenzoyl) ethane (500 mg) was reduced to the diol with lithium aluminum hydride which in turn was dissolved in 7 ml of pyridine and treated with 500 mg of $P_2S_5$ and heated at 70° C. for 2 hours. The reaction mixture was poured to ice-water and extracted with 3×30 ml of methylene chloride. The organic layer was washed with water, 5% HCL, saturated sodium bicarbonate solution and dried over sodium sulfate. Filtration and evaporation gave 366 mg of solid residue. 10 mg of this residue was separated on HPLC (mobile phase 30% ethyl acetate in hexane, solid support partisil 10/50) to yield trans-2,5-bis-(3,4-dimethoxyphenyl)tetrahydrothiophene (4.1 mg), m.p. 103°-5° C. NMR (CDCl$_3$) δ2.3-2.6(4H, m, —CH$_2$CH$_2$—), 3.90 and 3.94 (6H each, s, 2×OCH$_3$), 4.84 (2H, t, —CH—S—CH—) 6.8-7.4 (6H, m, Ar—H) and cis-2,5-bis-(3,4-dimethoxyphenyl)tetrahydrothiophene (5 mg, m.p. 107°-108° C.). NMR (CDCl$_3$) δ2.18-2.44(4H, m, —CH$_2$CH$_2$—), 3.88 (12H, s, 4×OCH$_3$), 4.66 (2H, t, J=5.5 Hz, —CH—S—CH—), 6.84-6.92 (6H, m, Ar—H)

Using a similar procesure, 2.0 g of 1,2-bis-(3,4,5-timethoxyphenyl)ethane was reduced with lithium aluminum hydride and treated with 2.0 g of $P_2S_5$ in 20 ml pyridine at 90° C. to yield 85.3 mg of trans-2,5-bis (3,4,5-trimethoxyphenyl) tetrahydrothiophene, m.p. 133°-134° C. NMR (CDCl$_3$) δ2.04-2.70 (4H, m, —CH$_2$CH$_2$), 3.87 (6H, s, 2×OCH$_3$), 3.92 (12H, s, 4×OCH$_3$), 4.84 (2H,t,—CH—S—CH—), 6.75 (2H, s, Ar—H)

EXAMPLE 2

3α,4β-dimethyl-2β,5β-bis(3,4-dimethoxyphenyl)-tetrahydrothiophene

One gram of racemic-2,3-bis-(3,4-dimethoxybenzoyl) butane was reduced to the diol with lithium aluminum hydride and then heated with 1.0 g $P_2S_5$ in 10 ml of dry pyridine at 100° C. for 1 hr. The contents were poured to 150 ml of water and extracted with 3×50 ml of methylene chloride. The combined methylene chloride layer was washed with water, 1N HCL, 10% NaOH and dried over sodium sulfate. Evaporation gave 0.65 g of colorless oil. 100 mg of this oil was fractionated by HPLC (mobil phase 35% ethylacetate in hexane, solid support partisil 10/50). The front running band (4.1 mg) was collected and identified as 3α,4β-dimethyl 2α,5β-bis-(3,4-dimethoxgphenyl)tetrahydrothiophene. NMR CDCl$_3$) 0.97 (6H, d, J=8 Hz, 2×CH$_3$), 3.88 and 3.91 (6H each, s, 2×OCH$_3$), 4.25 (2H, d, j=12 Hz, —CH—S—CH—), 6.5-7.2 (6H, m, Ar—H). Then the major fraction (30.3 mg, m.p. 98°-99° C.) was collected and characterized as 3α,4β-dimethyl-2α,5β-bis-(3,4-dimethoxyphenyl)tetrahydrothiophene NMR (CDCl$_3$) δ0.70 (3H, s, CH$_3$), 0.90 (3H, s, CH$_3$), 3.89 and 3.92 (6H each, s, OCH$_3$), 4.03 (1H, d, J=10 H$_z$, 5-H), 4.50 (1H, d, J=6.8 Hz, 2-H), 6.8-7.2 (6H, m, Ar—H).

EXAMPLE 3

2-(3,4,5-Trimethoxyphenyl)-5-(5,6-dimethoxypyridyl)-tetrahydrothiophene

Step A: Preparation of 1-(3,4,5-trimethoxybenzoyl)-2-(5,6-dimethoxy-3-nicotinoyl)ethane 5,6-Dimethoxy-pyridyl-3-carboxaldehyde (9 g), 12.6 g 3,4,5-trimethoxyphenyl vinyl ketote, 2.0 g 3-ethyl-5-(2-hydroxyethyl)-4-methylthiazolium bromide, 300 ml ethanol were refluxed for 30 minutes and to that 7.0 g triethyl amine added and refluxing continued for 24 hours. Upon cooling nice, tan, flaky, glittering crystals form. Yield 12.5 g, m.p. 133°-4° C.

Step B: Preparation of 1-(3,4,5-trimethoxyphenyl)-1,4-dihydroxy-4-(5,6-dimethoxy-3-pyridyl)-butane 1-(3,4,5-trimethoxybenzoyl)-2-(5,6-dimethoxy-3-nicotinoyl)ethane (12.0 g) in 200 ml methanol was treated with 4×1 g of NaBH$_4$ and refluxed for 1 hour. The solvent was removed and the residue dissolved in ethyl acetate, filtered through silica (or washed with water) and solvent removed by distillation to yield 12.1 g of 1-(3,4,5-trimethoxyphenyl)-1,4-dihydroxy-4-(5,6-dimethoxy-3-pyridyl)butane as colorless oily residue.

Step C: Preparation of 2-(3,4,5-trimethoxyphenyl)-5-(5,6-dimethoxypyridyl)-tetrahydrothiophene 1-(3,4,5-trimethoxyphenyl)-1,4-dihydroxy-4-(5,6-dimethoxy-3-pyridyl)butane (4 g), 4 g 2,4-bis-(4-methoxyphenyl)-2,4-dithioxo-1,3,2,4-dithiadiphosphetane or $P_2S_5$-pyridine complex and 20 ml of pyridine was heated at 90° C. for 1 hour, solvent distilled off and residue dissolved in MeCl$_2$ and extracted 3× with 10% NaOH. The organic layer was dried, filtered through silica and evaporated to yield 1.4 g of oily residue. 500 mg of this residue was chromatographed (HPLC, EtOAc:Hex (40:60), Whatman Magnum 20 Column) and the peak at retention time of 62 minutes (flow 10 ml/minute) was collected to yield 216 mg of trans 2-(3,4,5-trimethoxyphenyl)-5-(5,6-dimethoxypyridyl)tetrahydrothiophene.

What is claimed is:

1. A compound of formula

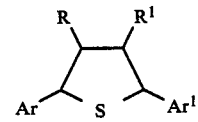

wherein R and R$^1$ independently are
 (a) hydrogen;
 (b) lower alkyl or cycloalkyl of 1-6 carbon atoms;
 (c) haloloweralkyl;
 (d) halo;
Ar and Ar$^1$ are the same or different from each other and are
phenyl or substituted phenyl of formula

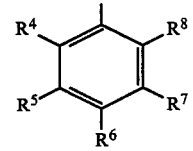

where R$^4$-R$^8$ independently represent H, R$^2$O—, R$^2$S—, R$^2$SO, R$^2$SO$_2$—, CF$_3$O—, CF$_3$S—, CF$_3$SO—, CF$_3$SO$_2$—, R$^2$R$^3$N—, —NR$^2$COR$^3$, —OCONH$_2$, —OCH$_2$CO$_2$R$^2$, —SO$_2$NR$^2$R$^3$, —CO$_2$R$^2$, —CONR$^2$R$^3$, —CR$^2$R$^3$R$^4$, —NR$^2$SO$_2$R$^3$, COR$^2$, NO$_2$, or CN or R$^4$-R$^5$, R$^5$-R$^6$, R$^6$-R$^7$ and R$^7$-R$^8$ are joined together forming a bridge with the proviso that Ar and Ar$^1$ cannot be simultaneously phenyl, 2. The compound of claim 1 wherein the compound is of formula:

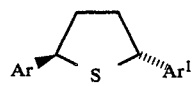

3. A pharmaceutical composition for treating a disease or a disorder mediate by PAF comprising a pharmaceutical carrier and a therapeutically effective amount of a compound of formula:

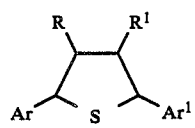

wherein R and R$^1$ independently are
 (a) hydrogen;
 (b) lower alkyl or cycloalkyl of 1-6 carbon atoms;
 (c) haloloweralkyl;
 (d) halo;
Ar and Ar$^1$ are the same or different from each other and are
phenyl or substituted phenyl of formula

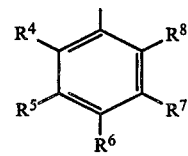

where R$^4$–R$^8$ independently represent H, R$^2$O—, R$^2$S—, R$^2$SO; R$^2$SO$_2$—, CF$_3$O—, CF$_3$S—, CF$_3$SO—, CF$_3$SO$_2$—, R$^2$R$^3$N—, —NR$^2$COR$^3$, —OCONH$_2$, —OCH$_2$CO$_2$R$^2$, —SO$_2$NR$^2$R$^3$, —CO$_2$R$^2$, —CONR$^2$R$^3$, —NR$^2$SO$_2$R$^3$, COR$^2$, NO$_2$, or CN or R$^4$-R$^5$, R$^5$-R$^6$, R$^6$-R$^7$ and R$^7$-R$^8$ are joined together forming a bridge wherein with the proviso that Ar and Ar$^1$ cannot be simultaneously phenyl.

4. The composition of claim 3 wherein the compound is of formula

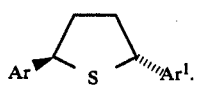

5. A method for the treatment of a disease or a disorder mediated by PAF comprising administering to a mammalian species in need of the treatment a therapeutically effective amount of a compound of formula:

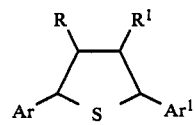

wherein R and R$^1$ independently are
 (a) hydrogen;
 (b) lower alkyl or cyaloalkyl of 1-6 carbon atoms;
 (c) haloloweralkyl;
 (d) halo;
 (e) COOH;
 (f) CONR$^2$R$^3$ wherein R$^2$ and R$^3$ independently represent C$_{1-6}$ alkyl and hydrogen;
 (g) COOR$^2$;
 (h) loweralkenyl;
 (i) —COR$^2$;
 (j) —CH$_2$OR$^2$;
 (k) loweralkynyl;
 (l) —CH$_2$NR$^2$R$^3$;
 (m) —CH$_2$SR$^2$;
 (n) =O; or
 (o) —OR$^2$;
Ar and Ar$^1$ are the same or different from each other and are
phenyl or substituted phenyl of formula

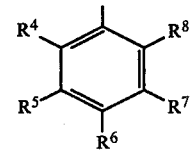

where R$^4$–R$^8$ independently represent H, R$^2$O—, R$^2$S—, R$^2$SO, R$^2$SO$_2$—, CF$_3$O—, CF$_3$S—, CF$_3$SO—, CF$_3$SO$_2$—, R$^2$R$^3$N—, —NR$^2$COR$^3$, —OCONH$_2$, —OCH$_2$CO$_2$R$^2$, —SO$_2$NR$^2$R$^3$, —CO$_2$R$^2$, —CONR$^2$R$^3$, —CR$^2$R$^3$R$^4$, —NR$^2$SO$_2$R$^3$, COR$^2$, NO$_2$, or CN or R$^4$-R$^5$, R$^5$-R$^6$, R$^6$-R$^7$ and R$^7$-R$^8$ are joined together forming a bridge.

6. The method of claim 5 wherein the compound is a stereoisomer of formula:

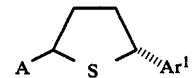

7. The compound of claim 1 which is trans-2,5bis(3,4,5-trimethoxyphenyl)tetrahydrothiopene.

8. The composition of claim 3 wherein the compound is trans-2,5-bis(3,4,5-trimethoxyphenyl)tetrahydrothiophene.

9. The method of claim 3 wherein the compound to be administered is trans-2,5-bis(3,4,5-trimethoxyphenyl)tetrahydrothiophene.

* * * * *